United States Patent [19]

Braude

[11] 4,382,027
[45] May 3, 1983

[54] PURIFICATION OF HUMAN IMMUNE INTERFERON

[75] Inventor: Irwin A. Braude, Burke, Va.

[73] Assignee: Meloy Laboratories, Inc., Springfield, Va.

[21] Appl. No.: 293,775

[22] Filed: Aug. 18, 1981

[51] Int. Cl.$^3$ .................. A61K 45/02; C07G 7/00
[52] U.S. Cl. .................................. 260/112 R; 424/85
[58] Field of Search .............. 424/85; 260/112 R; 435/68, 811

[56] References Cited

U.S. PATENT DOCUMENTS 4,168,261 9/1979 Edy .................................. 424/85
4,314,935 2/1982 Uemura et al. .................. 424/85

OTHER PUBLICATIONS

Yip, Y., et al., Proc. Natl. Acad. Sci., vol. 78, pp. 1601–1605, 1981.

Chemical Abstract, vol. 93, p. 321, Abst. No. 218752, 1980.

Primary Examiner—Blondel Hazel

[57] ABSTRACT

Disclosed is a process for the purification of crude immune interferon to a near homogeneous preparation which comprises: (a) adsorbing the crude interferon onto a column containing Controlled Pore Glass beads and eluting with ammonium sulfate, (b) adsorbing the interferon containing eluant onto a column containing either Concanavalin A-Sepharose, lentil lectin-Sepharose or pea lectin-agarose and eluting with a buffer containing a sugar, (c) adsorbing the interferon containing eluant onto a column containing Heparin-Sepharose or Procian Red-agarose and eluting with a high salt content buffer, and (d) treating the interferon containing eluant in a gel-filtration column equilibrated in high salt to obtain a solution of immune interferon that is nearly homogeneous.

17 Claims, No Drawings

PURIFICATION OF HUMAN IMMUNE INTERFERON

BACKGROUND OF THE INVENTION (1) Field of the Invention

This invention relates to the purification of human immune interferon. More particularly, the invention relates to a process for the purification of crude human immune interferon from induced human peripheral blood leukocytes by a series of steps to remove contaminants and yield a near homogeneous interferon preparation.

Interferon is a glycoprotein whose synthesis in cells is principally induced by viruses or mitogens. Interferons are classified into three major species designated IFN-α (leukocyte), IFN-β (fibroblast), IFN-γ (immune). Leukocyte and fibroblast interferons are induced by viruses or synthetic polynucleotides. Immune-type interferons are usually induced in primed lymphocytes by a specific antigen or in unprimed lymphocytes by T-cell mitogens. The thus produced interferons are associated with a variety of contaminants which include proteins and are referred to herein as "crude interferon."

(2) The Prior Art

Purification and characterization of interferons have been studied extensively and the subject has been reviewed recently in "The Interferon System," William E. Stewart II, Springer-Verlag, New York, N.Y. (1979). Among the various procedures for purifying human immune interferon is the procedure described by Langford, et al., in "Large-Scale Production and Physicochemical Characterization of Human Immune Interferon," Infection and Immunity, Vol. 26, pp. 36–41 (1979), who studies the use of Controlled Pore Glass (CPG) adsorption chromatography and gel-filtration chromatography for purifying HuIFN-γ. Another purification procedure is taught by Wiranowska-Stewart, et. al., in "Production, Partial Purification and Characterization of Human and Murine Interferons-Type II," Molecular Immunology, Vol. 12, pp. 625–623, (1980), which describes the use of CPG-adsorption chromatography and poly (U) Sepharose affinity chromatography. A third procedure was published by de Ley, et. al., in "Interferon Induced in Human Leukocytes by Mitogens: Production, Partial Purification and Characterization," European J. of Immunology, Vol. 10, pp. 877–833 (1980), describes the use of Controlled Pore Glass adsorption chromatography and eluting from the column with an ethylene glycol solution and gel-filtration chromatography. A fourth procedure by Yip, et. al., entitled "Partial Purification and Characterization of Human (Immune) Interferon," was published in Proc. Nat'l Acad. Sci., U.S.A., Vol. 78, pp. 1601–1605 (1981), where the use of Controlled Pore Glass adsorption chromatography, Concanavalin-A Sepharose affinity chromatography and gel-filtration chromatography are described.

SUMMARY OF THE INVENTION

The invention provides methods for purifying crude immune interferon produced from mitogen induced human peripheral blood leukocytes. Purification of the crude interferon includes the steps of interacting the crude interferon with one or more affinity resins in a single or series of successive steps each leading to a greater degree of purification.

The present invention in a preferred embodiment comprises a process for the purification of crude immune interferon to a near homogeneous preparation which comprises: (a) adsorbing the crude interferon onto a column containing Controlled Pore Glass beads and eluting with ammonium sulfate, (b) adsorbing the interferon containing eluant onto a column containing either Concanavalin A-Sepharose, lentil lectin-Sepharose or pea lectin-agarose and eluting with a buffer containing a sugar, (c) adsorbing the interferon containing eluant onto a column containing Heparin-Sepharose or Procian Red-agarose and eluting with a high salt content buffer, and (d) treating the interferon containing eluant in a gel filtration column, equilibrated in high salt, to obtain a solution of immune interferon that is nearly homogeneous.

Using the purification process of this invention unlysed cells may be used to produce crude immune interferon. If unlysed red blood cells remain in the cell culture used to produce the interferon, the crude interferon must be treated with sufficient tris (hydroxymethyl) amino methane to bring the concentration to 500 mM and buffered to pH 9.5 prior to purification. Additionally, ammonium sulfate is used to elute from the Controlled Pore Glass beads rather than ethylene glycol. This eliminates the necessity of changing buffers when going from one purification step to the next which means the purification steps may be made continuous. In addition, using ammonium sulfate in place of the ethylene glycol permits the immune interferon to remain stable.

It is the general object of this invention to provide a process for purifying crude human immune interferon which is efficient and functional and yields a near homogeneous interferon preparation. Another object of this invention is to provide a process for purifying crude human immune interferon which may perform continuously. Yet another objective of this invention is to provide a purification process which may use a crude interferon starting material produced from cell cultures containing lysed or unlysed red cells. A still further objective of this invention is to utilize a series of affinity columns for step-wise purification of crude immune interferon with columns which are interchangeable. An even further object of this invention is to utilize ammonium sulfate as a CPG-eluant. Another object of this invention is the use of lentil- or pea lectin resins as an absorbent. Yet a further object of this invention is the use of an affinity column containing Heparin-Sepharose or Procian Red-agarose as an adsorbent. Still another object of this invention is the use of high salt eluants in the gel-filtration procedures.

Other objects features and advantages will be seen from the following detailed description of the invention.

DETAILED DESCRIPTION OF THE INVENTION

The process of this invention describes a method for purifying crude immune interferon. Crude immune interferon may be obtained from human peripheral blood leukocytes by a number of well known techniques. Among the methods which may be used are those methods described in the prior art articles described herein.

In accordance with a preferred embodiment of this invention, a solution of crude immune interferon produced from cell cultures containing unlysed red blood cells and having at least 5000 units/ml is adjusted to 500 mM with tris (hydroxymethyl) amino methane and the pH is brought to about pH 9.5–9.7 with 12 N hydrochloric acid.

The solution of crude interferon is contacted with Controlled Pore Glass for a period of time sufficient to accomplish equilibrated adsorption of the crude interferon to the beads in the presence of a neutral pH buffer, such as phosphate buffered saline at about pH 7.2. It should be understood that the adsorption may be carried out in any appropriate vessel, but it is preferable to use a chromatographic column.

Controlled Pore Glass beads are composed of borosilica glass varying in mesh and bead size. Commercially available sources for Controlled Pore Glass beads include Corning and Electro-Nucleonics, Inc. Those beads provided by Electro-Nucleonics, Inc. are available in three sizes (80/120; 120/200; 200/400) and eleven pore sizes (75 to 300 Angstoms). The Controlled Pore Glass beads such as those marketed by Electro-Nucleonics, Inc. (for example, mesh size 120/200) are loaded into a column, for example, 2.5 by 30 cm. The size of the column is a function of the amount of interferon to be loaded. The solution of crude interferon is passed through the column with the interferon binding itself to the beads and the unadsorbed material passing unretarded through the column.

The glass beads having interferon adsorbed thereon are first washed with a chemically compatible buffer until the optical density of the elute at 280 nm is about 0. This washing serves to remove unbound contaminants from the glass beads. An example of a suitable chemically compatible buffer is an aqueous solution containing tris (hydroxymethyl) amino methane at a concentration of 500 mM and buffered to about pH 9.5. The glass beads having interferon adsorbed thereon are next washed with a neutral pH buffer, such as phosphate buffered saline (0.15 M, pH 7.2) until the eluant optical density at 280 nm is about 0. Another eluant is passed through the glass beads to selectively dissociate the immune interferon from its bead adsorption site. The partially purified immune interferon is eluted from the beads with an aqueous solution of 2 M ammonium sulfate at pH about 9.0. Althought this preferred embodiment contemplates a final pass with an aqueous ammonium sulfate solution at pH 9.0, other concentrations can certainly be used. For example, the final pass volume desirably is an inorganic salt solution from about 1.5 to about 2.5 M in about 50% ammonium sulfate.

If further purification is desired, the interferon-containing solution may be passed directly to another purification step when the interferon-containing solution is contacted with another absorbent for a period of time sufficient to accomplish equilibrated adsorption of the interferon to the absorbent in the presence of a neutral pH buffer. The absorbents useful for this purification include Concanavalin A-Sepharose lentil lectin-Sepharose and pea lectin-agarose. Any suitable adsorption vessel may be used, but preferably the resin absorbent is packed in a chromatographic column and the interferon-containing solution is passed therethrough. The neutral pH buffer may be phosphate buffered saline (PBS). PBS is a standard biological solvent composed of 0.9% NaCl in water, adjusted to a pH 7.2 with phosphate buffer.

After the interferon has been loaded onto the absorbent, the absorbent is first washed with 2 M ammonium sulfate (pH 9.0) until the optical density at 280 nm is about 0 to remove the soluble or loosely bound contaminants. Next, it is desirable to remove some of the adsorbed contaminants and so the absorbent is washed with a neutral pH buffer, such as PBS, until the eluate optical density is about 0.

To remove the immune interferon from the absorbent, elution is carried out with a neutral pH buffer containing a sugar. A suitable buffer is phosphate buffered saline containing from 0.1 M to 2.0 M alpha-methyl D-mannoside or 1-methyl D-glucoside. The interferon-containing eluant may be used at that purity or may be even further purified. It should also be appreciated that this purification step may be carried out prior to the Controlled Glass Pore bead purification step.

If further purification is desired, the partially purified interferon may be treated to an additional purification step.

In this purification step an absorbent resin of either Heparin-Sepharose (H/S) or Procian-Red agarose is equilibrated in a suitable neutral pH buffered solution, such as PBS for a period of time sufficient to accomplish equilibrium. The interferon containing eluant is loaded directly onto the material. As in the other purification steps, any suitable vessel may be used, but it is preferable to use a chromatographic column.

After the interferon has been loaded onto the matrix, the matrix is washed with first a neutral pH buffered solution, such as PBS, containing about 1 M alpha-methyl D-mannoside or 1-methyl D-glucoside until the eluate optical density at 280 nm is about 0. In order the remove some of the bound contaminants, the matrix is washed with PBS until the optical density at 280 nm is about 0. The partially pure interferon is eluted from the matrix with a second neutral pH buffer, such as PBS, containing a high concentrated salt, for example, about 2 M sodium chloride.

The interferon rich fraction may be collected and used as is or may be even further purified.

The interferon-rich elution fraction is next loaded on a gel-filtration column network (Biogel P100 or P150 column, Bio-Rad, Richmond, Calif.) equilibrated in two 2.5×96 cm. columns hooked in series and in a neutral pH buffered solution containing a high salt concentration. The neutral pH buffered solution is preferably phosphate buffered saline having a salt concentration of about 2 M sodium chloride. The near pure interferon is eluted from the gel-filtration column with 2 M NaCl in phosphate-buffered saline. The exact concentration of the NaCl solutions is not critical. The purified immune interferon obtained is a near homogeneous preparation.

It should be specifically pointed out that the order of purification steps is not critical and may be changed as desired. Past purification techniques have used eluants which must be removed prior to a further purification step or eventually inactivate the interferon. On the other hand, the process of this invention provides for a continuous process.

An alternative embodiment of the process of this invention provides yet an additional purification step using phenyl-Sepharose as the affinity ligand. This step offers the advantages of converting the immune interferon containing 2 M sodium chloride to a buffer which contains low concentrations of sodium chloride and is therefore physiologically compatible.

The procedure results in both purification and concentration of interferon activity. The specific activity of the starting material on the average was $10^2$ interferon units/mg, while that of the gel-filtered material was between $10^{7.5}$ and $10^{8.0}$ units/mg, with the peak fraction containing greater than $10^6$ units/ml. Thus, a $10^6$-fold increase in specific activity was obtained. Table I demonstrates the purification and recovery of human immune interferon by individual resins.

TABLE I
PURIFICATION OF HUMAN IMMUNE INTERFERON

| Resin | Specific Activity ($\log_{10}$ Units/mg) | Purification Factor | Recovery (%) |
|---|---|---|---|
| [a]CPG | 5.8 | 1600 | 103 |
| [b]Lectin | 7.1 | 200 | 84 |
| [a]Hep.-Seph. | 4.1 | 146 | [d]347 |
| [c]Gel-Filtration | N.D. | N.D. | N.D. |

[a]Starting with crude material.
[b]Starting with CPG - Purified material.
[c]It is not practical to load crude immune interferon onto a gel-filtration column. N.D. means "Not Determined."
[d]There can be at least a three-fold variation in the biological assay.

The preferred embodiments of this invention are further illustrated by the example which follows.

EXAMPLE 1

A crude interferon preparation produced from a cell culture containing unlysed red blood cells was purified as described. The following solutions were prepared: A solution of 500 mM tris (hydroxymethyl) amino methane at pH 9.5, referred to as tris. A solution of 2 M ammonium sulfate at pH 9.0 (w/NH$_4$OH). A neutral pH buffered solution of phosphate buffered saline (PBS) at pH 7.2 having a 1 M solution of alpha-methyl D-mannoside. A phosphate buffered saline solution (PBS) at pH 7.2 containing 2 M sodium chloride (NaCl).

A 2.6×30 cm chromatographic column was loaded with Controlled Pore Glass beads (CPG) (=160 ml bed colume). A 1.6×16 cm chromatographic column was loaded with Concanavalin A-Sepharose (Con A) (=32 ml bed volume) and a 1.6×8 cm chromatographic column was loaded with Heparin-Sepharose (H/S) (=16 ml bed volume). These three columns were equilibrated with phosphate buffered saline (PBS). Two gel-filtration columns, 2.6×94 cm, containing P-100 (=400 ml bed volume) were prepared and equilibrated with 2 M NaCl in PBS and hooked up in series.

The purification was carried out as follows: A solution of centrifuged crude immune interferon was adjusted to 500 mM with powdered tris. The adjusted crude interferon was loaded onto the CPG column at a flow rate of =500 ml/hr (=94 ml/cm$^2$/hr). The column was monitored at 2.0AU and the unbound material collected into a beaker. The CPG column was washed with a 500 mM tris solution, pH 9.5, until the optical density (OD$_{280}$) was 0. The column was monitored at 2.0AU and the unbound material collected. The column is washed with PBS until OD$_{280}$ returns to baseline. (Flow rate 80 ml/hr overnight). The eluted material is collected into a second beaker. The CPG column was eluted with 2 M ammonium sulfate at pH 9.0 at a flow rate of 24 ml/hr, and 10 ml fractions were collected. When second peak began to appear, the inlet of the Con A column was connected into the outlet of the monitor and the outlet of the Con A column into the fraction collector. The CPG column eluted onto the Con A column at a flow rate of 24 ml/hr. (12/cm$^2$/hr thru Con A). The column was monitored as above and 10 ml fractions collected until the OD$_{280}$ reached the baseline.

The CPG column was disconnected from the monitor and the monitor connected to the Con A column. The Con A column was washed with PBS until OD$_{280}$ returned to baseline. The flow rates and collections were monitored as above. The inlet of the H/S column was connected to the outlet of the monitor and the outlet of the H/S to the fraction collector. The Con A column was eluted with the PBS sugar solution. The flow rate and collect were monitored as above until the OD$_{280}$ returned to baseline.

The Con A column was disconnected from the monitor and the H/S connected to the monitor. The H/S column was washed with PBS until OD$_{280}$ returned to baseline. The flow rate and collection were monitored as above. The H/S column was eluted with 2 M NaCl in PBS, pH 7.2 until OD$_{280}$ returned to baseline. The flow rate was monitored as above and 3 ml fractions were collected. The H/S peak fractions were selected by OD$_{280}$ then collected and pooled.

The pooled material was loaded onto the drained bed of the first P-100 column at 20 ml/hr by gravity (=80% bed height pressure head). After sample was loaded, the sides of column were washed with 2 M NaCl in PBS, pH 7.2. The flow was stopped and the column topped off with PBS. The flow was then opened and the column run at 24 ml/hr in PBS, pH 7.2 with 2 M NaCl. The system was monitored at 0.5AU and 10 ml fractions were collected. The results in Table II show the degree of purification and recovery of human immune interferon when purified by the sequential purification techniques described above.

TABLE II

| Description | Titer ($\log_{10}$ units/ml) | Volume (ml) | Recovery (%) | Protein (mg/ml) | Specific Activity ($\log_{10}$ units/mg) |
|---|---|---|---|---|---|
| Crude | 3.7 | 3600 | NA | 18.46 | 2.4 |
| P-100 Column: | | | | | |
| Fraction 123 | 6.2 | 9.5 | 84 | 0.020 | 7.9 |
| Fraction 124 | 6.2 | 9.5 | 84 | 0.016 | 8.0 |

While the invention has been described in terms of preferred embodiments constituting the best mode known to the applicants at the time of this application, various changes may be made in the invention without departing from the scope thereof, which is defined by the following claims.

What is claimed is:

1. A process for purifying crude human immune interferon which comprises:
    (a) contacting a solution of crude interferon with Controlled Pore Glass beads for a period of time sufficient to accomplish equilibrated adsorption of the crude interferon to the beads in the presence of a neutral pH buffer, washing the glass beads having interferon adsorbed thereon with a chemically compatable buffer to remove the unbound contaminant until the optical density of the eluate at 280 nm is about 0, washing the glass beads having interferon adsorbed thereon with a neutral pH buffer solution until the optical density at 280 nm is about 0, eluting the adsorbed immune interferon from the glass beads with an ammonium sulfate solution;
    (b) contacting the solution of interferon with an absorbent selected from the group consisting of Concanavalin A-Sepharose, lentil lectin-Sepharose and pea lectin-agarose for the period of time sufficient to accomplish equilibrated adsorption of the interferon to the absorbent in the presence of a neutral pH buffer, washing the absorbent having interferon adsorbed thereon from the soluble fraction with ammonium sulfate until the optical density of the eluate at 280 nm is about 0, washing the absorbent with a neutral pH buffer until the optical density of the eluate at 280 nm is about 0, eluting the adsorbed interferon with a buffer containing a member of the group consisting of alpha-methyl D-mannoside and 1-methyl D-glucoside;

(c) contacting the interferon with a member selected from the group consisting of Heparin-Sepharose or Procian Red-agarose for a period of time sufficient to accomplish equilibrated adsorption of the interferon to the member equilibrated in a neutral pH buffered solution, washing the member containing adsorbed interferon thereon with first a neutral pH buffered solution containing a sugar selected from the group consisting of alpha-methyl D-mannoside and 1-methyl D-glucoside to remove the unbound material until the optical density of the eluate at 280 nm is about 0, washing with a neutral pH buffered solution until the optical density is about 0 to remove the bound material eluting the adsorbed interferon with a second neutral pH buffered solution containing a highly concentrated salt, and;

(d) further purifying by subjecting the elution fraction to gel-filtration treatment equilibrated in a neutral pH buffered solution containing a highly concentrated salt, and eluting whereby the solutes within the elution fractions are separated according to their molecular weights; and collecting the solute fraction containing a near homogeneous interferon preparation.

2. The process according to claim 1, wherein the steps are carried out continuously.

3. The process according to claim 1, wherein the steps are carried out sequentially.

4. The process according to claim 1, wherein step (b) is carried out prior to step (a).

5. The process according to claim 1, wherein the sequence of steps is from step (c) to step (b) to step (a) to step (d).

6. The process according to claim 1, wherein the crude interferon is produced from cell cultures containing unlysed red blood cells and added thereto is sufficient tris (hydroxymethyl) amino methane to bring the concentration to 500 mM, the solution is then buffered to pH 9.5 to 9.7 prior to beginning purification.

7. The process according to claim 1, wherein the Controlled Pore Glass beads have a mesh size designated as 120/200 or 200/400.

8. The process according to claim 7, wherein the crude interferon solution is passed through a chromatographic column packed with Controlled Pore Glass beads.

9. The process according to claim 1, wherein the adsorbed interferon in step (a) is eluted from the glass beads by first washing the beads with tris (hydroxymethyl) amino methane until the optical density of the eluate at 280 nm is about 0; further treating the beads to sequential passes with a volume of neutral pH buffered solution to wash the beads of contaminants; treating the beads to a final pass volume of ammonium sulfate which selectively dissociates the immune interferon from its bead adsorption site, and collecting the final pass volume comprising the interferon-containing elution fraction.

10. The process according to claim 1, wherein the chemically compatible buffer is tris (hydroxymethyl) amino methane at a concentration of 500 mM and pH 9.5 and the neutral pH buffer is phosphate buffered saline and the final pass volume is 2 M ammonium sulfate at about pH 9.0.

11. The process according to claim 1, wherein in step (b) the neutral pH buffer is phosphate buffered saline, the adsorbed interferon eluted by first washing with 2 M ammonium sulfate; further washed with sequential volumes of a neutral pH buffered solution to wash the adsorbent free of contaminants, until the optical density of the eluant at 280 nm is about 0; treating the absorbent to a final pass volume of phosphate buffered saline containing from 0.1 M to 2 M alpha-methyl D-mannoside of 1 methyl D-glycoside, and collecting the final pass volume containing the interferon fraction.

12. The process according to claim 11, wherein the interferon is passed through a chromatographic column packed with absorbent.

13. The process according to claim 1, wherein in step (c) said first neutral pH buffered solution is phosphate buffered saline containing sugar selected from the group consisting of alpha-methyl D-mannoside and 1 methyl D-glucoside, and said second neutral pH buffered solution is phosphate buffered saline containing about 2 M sodium chloride, and collecting the final pass volume containing the interferon.

14. The process according to claim 1, wherein in step (d) said gel-filtration treatment includes equilibrating the column with phosphate buffered saline containing 2 M sodium chloride, and eluting with about 2 M sodium chloride in phosphate buffered saline to achieve separation of interferon from the solutes.

15. The process according to claim 1, wherein the thus collected interferon is further contacted with phenyl-Sepharose for a period of time sufficient to accomplish equilibrated adsorption of the interferon to the phenyl-Sepharose, and eluting the thus treated interferon with low salt buffers.

16. A process for purifying crude human immune interferon which comprises, contacting a solution of crude interferon with a resin from the group consisting of Heparin-Sepharose or Procian-Red agarose for a period of time sufficient to accomplish equilibrated adsorption of the interferon to the resin, washing the resin interferon adsorbed thereon with phosphate buffered saline containing sugar selected from the group consisting of alpha-methyl D-mannoside, and 1-methyl D-glucoside until the optical density at 280 nm is about 0, washing with phosphate buffered saline solution until the optical density at 280 nm is about 0, and eluting the adsorbed interferon with phosphate buffered saline containing 2 M sodium chloride.

17. In a process for purifying human immune interferon comprising contacting a solution of crude interferon with Controlled Pore Glass beads for a period of time sufficient to accomplish equilibrated adsorption of the crude interferon to the beads; separating the adsorbed interferon from the glass beads, the improvement comprising;

eluting the adsorbed human immune interferon from the Controlled Pore Glass beads with a solution containing ammonium sulfate.

* * * * *